United States Patent [19]

Metzger et al.

[11] Patent Number: 4,792,434
[45] Date of Patent: Dec. 20, 1988

[54] SAMPLE PREPARATION CHAMBER WITH MIXER/GRINDER AND SAMPLE ALIQUOT ISOLATION

[76] Inventors: Andre Metzger, (Le Verger), 12 Rue de Saules, 68300 St. Louis, France; Peter Grimm, Brunnmatt Str. 22, CH 4402 Frenkendork, Switzerland; Andre J. Nohl, 479 Wheller Rd., Menlo Park, Calif. 94025; Vance J. Nau, 22404 Riverside Dr., Cupertino, Calif. 95014

[21] Appl. No.: 942,198

[22] Filed: Dec. 16, 1986

[51] Int. Cl.$^4$ .......................... B01F 7/22; B01L 3/00; B28C 5/08
[52] U.S. Cl. .................................. 422/100; 422/101; 422/102; 422/283; 366/65; 366/168; 366/270; 366/279
[58] Field of Search .................. 422/99, 100, 101, 102, 422/283; 366/64, 65, 168, 270, 169, 279

[56] References Cited

U.S. PATENT DOCUMENTS 3,223,485 12/1985 Ferrari et al. .
3,259,743 7/1966 Pick et al. .
3,511,618 5/1970 Michaud et al. ................ 422/283 X

FOREIGN PATENT DOCUMENTS 0089937 3/1983 European Pat. Off. .

Primary Examiner—Barry S. Richman
Assistant Examiner—Lyn Kummert
Attorney, Agent, or Firm—Ron Fish

[57] ABSTRACT

There is disclosed a sample preparation chamber for a system for preparing samples of various compositions for assay by liquid chromatography. The sample preparation chamber is a container having a threaded cap and a threaded, lightweight, translucent plastic cup. A stirred/grinder shaft driven by a motor and connected to a propeller/grinder passes through the cap. The cap has a sloped bottom with a sump region, and a fill/empty pipe passes through the cap and has its outlet at or near the sump. A nozzle fill pipe arrangement allows the walls to be washed down as liquid is pumped into the cup. A second fill pipe with its outlet spaced up from the bottom of the cup is also used, and a sample metering valve having an inlet in said cup is present. The sample metering valve is used to isolate a known volume of the sample from the rest of the sample for release back into the cup after the remaining sample has been pumped to waste for purposes of diluting the known volume of sample to a known concentration.

14 Claims, 3 Drawing Sheets

SAMPLE PREPARATION CHAMBER WITH MIXER/GRINDER AND SAMPLE ALIQUOT ISOLATION

BACKGROUND OF THE INVENTION

The invention relates to the field of sample preparation systems for chemical assays, and, more particularly, to the field of sample preparation chambers or systems that are adapted to handle liquid, solid, granulated or highly viscous samples.

In many chemical processing facilities and laboratories there is a need to do chemical assays on chemical samples. Often these assays are done by means of gas or liquid chromatography. The form in which the samples for analysis come are many and varied. For most chromatography assays, diluted solutions of a homogeneous mixture of the sample and a diluent must be used. If the sample is a solid, it must first be dissolved. If the sample is a two phase liquid/liquid or liquid/solid combination, the mixture must be homogenized. If the sample is viscous, its viscosity must be reduced by dilution so that it may be pumped through the liquid chromatography column. All the samples must be diluted to a known concentration prior to pumping the diluted sample solution through the liquid chromatography column.

It is important in preparing samples for liquid chromatography and other types of assays to know the exact concentration of the sample being supplied to the assay. When dilution is being performed therefore, it is important to be able to isolate a known quantity of the sample. If the same container is to be used for a series of dilutions, it is also important to remove the rest of the sample from the container where the diluted sample is to be stored. To get exact concentrations, it is also necessary to be able to wash out the remnants of the sample from the various tubes in the system and off the walls of the sample container.

For solid samples it is important to be able to grind them to powder and to be able to add solvent to the powder before dissolving it in preparation for dilution to the desired concentration. For two phase samples it is advantageous to be able to use the same mechanism used for the grinding of the solid samples to mix the two phase samples to homogenize them.

Further, for any samples, particularly solid or viscous samples which are too viscous to pump. it is useful to have a sample container that is lightweight, detachable and portable so that it may be taken to the location of the sample and sample may be placed therein. The sample amount may be determined by weighing the cup before and after the sample has been placed therein. The sample container may then be filled with diluent to reduce the viscosity to a useable range.

The prior art sample preparation systems do not have all the capabilities noted above. Basically the prior art sample preparation systems are designed to handle only ideal samples which are homogeneous liquids. The ability to handle two phase samples, solid samples or very viscous samples has, heretofore been missing from the art. Further prior art sample preparation chambers do not include means to wash down the walls of the chamber prior to diluting the metered sample, or to isolate a fixed amount of sample immediately following homogenization.

SUMMARY OF THE INVENTION

According to the teachings of the invention there is provided a sample preparation chamber which is capable of being used to prepare many different types of samples for chemical assay, especially by liquid chromatography. The sample preparation chamber is comprised of a threaded, sloped bottom cup which is lightweight and transparent for holding and transporting the sample liquid or solid. The cup threads to a cap which serves to keep liquids in by a liquid seal between the cup flange and the mating cap flange. The detachability of the cup allows the cup to be removed and taken to the location of the sample so that a measured amount of sample may be placed therein if desired. Several elements pass through the cap. These elements include a drain pipe which extends to the lowest point in the sloped bottom of the cup and has a diameter which is large enough to pump viscous liquids through without excessive pressure. A second fill pipe also passes through the cap but does not extend to the bottom of the cup. This fill pipe may be used to pump liquid sample, solvents or diluent into the cup as may the larger fill pipe that extends to the bottom of the cup.

There is also a nozzle which extends through the cap which may be used to wash down the side walls of the cup. The nozzle is a propeller like structure in line with the fluid outlet of a pipe. To use this feature, the user pumps solvent or some other liquid through the pipe connected to the nozzle. The fluid flow causes the propeller or nozzle element to spin. This deflects fluid laterally out toward the side walls of the cup thereby washing down the walls.

The sample container also includes a stirring/grinding mechanism. This mechanism includes a motor driving a shaft which passes through the cap. The shaft is coupled to a propeller or other stirring structure which may or may not be suitable for grinding solid samples. The user may change the structure of the stirrer/grinder propeller to best suit the types of samples the user customarily prepares for assay. For some applications the user may prefer to substitute other types of mixers, such as ultrasonic mixers or high speed mixers both of which are commercially available.

A sample metering valve is also provided for allowing the user to isolate a known volume of sample from the rest of the material in the cup. This known volume may then be released back into the cup after the rest of the sample has been pumped to waste and, optionally, the walls have been washed down and the solvent pumped to waste.

DETAILED DESCRIPTION OF THE PREFERRED EMBODIMENT

Figure 1:
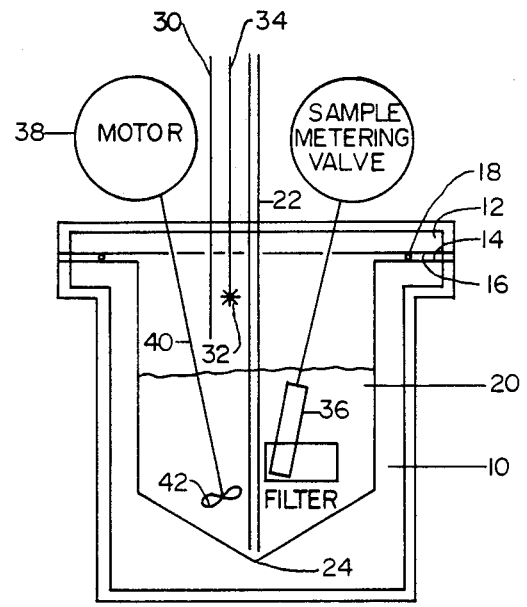
FIG. 1 is an elevation view of the sample container system of the invention.

FIG. 1 is an elevation view of the sample container system of the invention. The sample container is generally used as part of a sample preparation system which uses a pump capable of highly accurate delivery of fluid volumes. The sample container includes a cup 10 which, in the preferred embodiment is made of a transparent or translucent, lightweight chemically inert material. Depending upon the user's application, the cup may be made out of other materials as well where one or more of the above properties is not important. The cup is threaded or otherwise formed so that it may be mechanically attached to and supported by a cap 12. Typically, the cap will be attached to some solid support in the system, and will have a matching means of mechanical attachment to the cup. The manner of attachment to the cup is not critical to the invention, and any mechanical linkage which will withstand the weight and provide a seal which is adequate for the user's application will suffice.

The cup and the cap are shown in FIG. 1 as having mating surfaces 14 and 16 and a seal 18. The seal 18 may be any type of seal which will maintain the liquid 20 in the cup, or optionally may be omitted in some applications. Further, other designs may be used for sealing the structure in that mating surfaces 14 and 16 may be in the form of a tongue in groove seal or any other known structure.

The cup may have any thickness which will provide adequate structural strength for the sample types and application contemplated by the user. For a general purpose system where samples of many types are to be handled including solids, the cup 10 should have sufficient structural strength to withstand the forces which are involved in grinding a solid sample into a powder or smaller chunks in a dry state prior to the addition of solvent to dissolve the sample. A disposable version of the cup may be used where the cup consists of a thin disposable lining supported by a secondary stronger retaining structure. The bottom of the cup has a sump or lowest point where the last drops of a liquid collect. The exact configuration of the bottom is not critical as long as there is a lowest point 24 from which the liquid in the cup may be collected for pumping to waste. It is important to be able to pump as much as possible of the remaining sample out of the cup after the desired aliquot of sample has been isolated by the sample metering valve to be described below. This allows the final concentration of the sample to be closely controlled, by allowing the user to drain out all remaining sample before releasing the isolated, known volume of sample from the metering valve into the cup 10 and pumping in a known amount of diluent. If some unknown amount of sample was in the bottom of the cup which was not susceptible to being drained out or rinsed out because of the shape of the bottom of the cup, then the final concentration could not be controlled with good accuracy.

Figure 2:
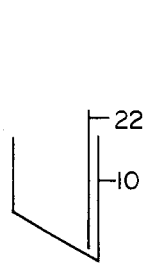
FIG. 2 shows in elevation and cross section the configuration of another shape for the cup bottom with the lowest point along an edge of the cup.
Figure 3:
FIG. 3 shows another shape for the bottom of the cup wherein a sump is centrally located with sloping bottom panels converging on the sump.
Figure 4:
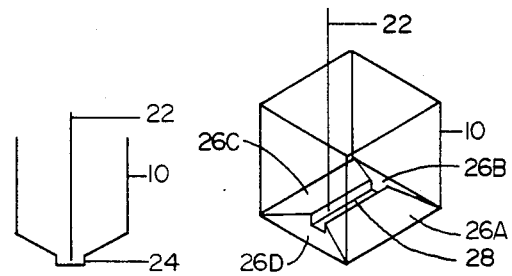
FIG. 4 shows another shape for the bottom of the cup wherein a slot is formed in the bottom of the cup with sloping bottom panels converging on the slot with the bottom of the slot being the lowest point of the bottom.

FIGS. 2 through 4 show some of the other possible bottom shapes for the cup 10. FIG. 2 shows, in elevation and cross section, one possible embodiment for the shape of the bottom of the cup. In this embodiment, the cup will have at least one straight edge and the lowest part of the bottom will be adjacent to this edge. The bottom of the cup slopes toward the low point adjacent to the straight edge. The other sides of the cup may have any desired shape. For that matter, the "straight" edge need not be straight at all, but, instead, may be wavy or curved. FIG. 3 shows in cross section and elevation another possible bottom configuration for the cup 10 using a well or sump in a sloped bottom where the bottom panels all slope toward the well. The cup may be cylindrical, curved, a polygon or rectangular for the embodiment of FIG. 3. The sump 24 may be round, curved, polygonal or rectangular. FIG. 4 shows in perspective another bottom configuration for the cup 10. In this embodiment, the bottom panels 26A through 26D all slope toward a slot 28 formed in the bottom. The slot 28 serves as a sump and the bottom of the slot is the lowest part of the bottom. Alternatively, a flat bottom cup could be used with the cup tilted on its side so that the bottom corner of the cup which is lowest could serve as the sump.

A fill/drain pipe 22 of relatively larger diameter passes through the cap 12 and extends down into the cup such that the opening of the fill/drain pipe is at or near the lowest point in the bottom. Preferably, the fill pipe opening is located as near as possible to the lowest point of the bottom to maximize the amount of sample which can be pumped out of the cup. The purpose of the larger diameter fill/drain pipe 22 is to allow the cup 10 to be emptied as quietly as possible and to allow heterogeneous slurries or viscous samples to be pumped into or out of the cup. In the preferred embodiment, there is a seal (not shown) around the fill/empty pipe where it passes through the cap 12.

Another fill pipe 30, which may be a smaller diameter than the fill/empty pipe 22, is provided to allow the user to pump in sample or diluent which is not so viscous as to hinder the process of pumping it through a small diameter tube. The fill pipe 30 does not extend all the way down to the bottom of the cup, but stops short of the bottom, and may be used to selectively sample a particular layer of a multiple phase system.

A nozzle 32 and fill pipe 34 together comprise the system which provides the ability to wash down the walls of the cup. When a viscous sample or any sample has been present in the cup and pumped or otherwise driven out to waste, resident sample or sample solution sticks to the walls of the cup.

Any residual sample adhering to the cup or tubing walls presents a source of contamination to the next step of the sample preparation process or the next sample processed and must therefore be removed. More specifically, the unknown residual sample or sample solution would present a source of contamination from one sample to the next, and a source of cumulative error when using the same vessel for successive sample prep steps.

To minimize the uncertainty created by the above situation, the nozzle 32 and fill pipe 34 are used. A suitable solvent which can dissolve the sample in question from the walls is pumped in via the pipe 34. This stream of solvent leaving the end of the fill pipe attached to the nozzle 32 causes the nozzle 32 to spin due to torsional forces present from the design of the nozzle 32. That is, the nozzle is shaped such that the force of liquid exiting in one direction off center from the main axis causes the nozzle to spin in the opposite direction. When the stream of solvent is forced through the nozzle, the nozzle spins thereby throwing solvent laterally against the walls of the cup. This washes down the walls of the cup to remove remaining sample stuck thereto. The solvent and remaining sample so removed and in solution in the solvent are then pumped to waste using the fill/empty pipe 22.

To provide a facility to mix two phase solvents, to grind solid samples to powder or smaller chunks, and to speed up the process of dissolving such samples in solvent, a mixer/grinder 38 is provided. This device includes a motor or other type of device capable of imparting a mixing action on the sample or sample solution. Such other types of devices include pneumatic motors, high speed mixers, ultrasonic probes, etc. The mixer/grinder 38 uses a propeller/grinding tool 42 attached to the end of the shaft 40 to do the mixing of liquids and the grinding of solid samples. The applicants believe that the invention may be the first general purpose sample preparation for liquid chromatography designed to allow processing of solid samples, slurries, or two phase liquid samples prior to the addition of solvent in order to put the sample in a solution suitable for passing through a liquid chromatography column. The user may use any type of mixer/homogenizer design which suits the type of samples the user normally processes. Designs for propellers and grinders which are suitable for various situations are known although they may be in other art areas. There is an optional seal (not shown) in the cap 12 through which the shaft 40 passes to maintain the liquid tight integrity of the sample preparation chamber during the turbulence created by the mixer/grinder 38. The design for such a seal is well known in the art.

To provide a facility for the taking of sample aliquots of known volume, there is a sample metering valve 36. This apparatus can take many forms some of which are more suitable for certain types of samples than others. The details of the different types of sample metering valves which are suitable for various types of samples are given in U.S. patent application entitled, "Sample Metering Valve for Sample Preparation System", Ser. No. 942,201, filed Sept. 16, 1986 and assigned to the assignee of the present application said application being hereby incorporated by reference. For completeness here, there will be given a description of two types of sample metering valves which are acceptable to practice the invention.

Figure 5:
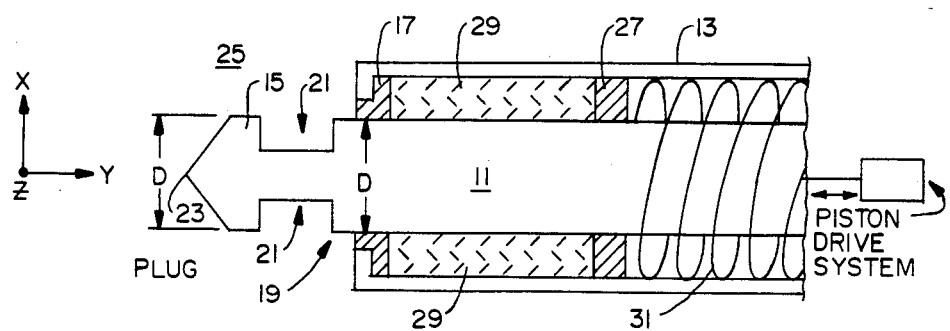
FIG. 5 is a cross sectional view of a sample metering valve for handling liquid samples and shown in the piston extended position.

Referring to FIG. 5, there is shown a cross sectional view of the sample metering valve of the preferred embodiment. A piston 11 is disposed within an open ended cylinder 13. The piston is typically metal with a chrome finish or is highly polished so as to have a smooth surface to minimize friction as the piston moves back and forth on the y axis. The piston has a T shaped end with a sealing plug 15 which has the same outside diameter D as the inside diameter of a seal 17 at the "open" end 19 of the cylinder. The piston 11 is shown in the extended position. In the retracted position of the piston 11, shown in FIG. 6, the sealing plug 15 is pulled back into the opening in the cylinder 13 so as to be in sealing contact with the sealing ring 17.

The piston 11 has a sample collecting recess 21 formed therein a small distance along the y axis away from the tip 23 of the piston. The purpose of the sample collecting recess 21 is to capture a known volume of material from the surrounding medium 25 when the piston is in the extended position. Therefore, the recess 21 must be machined or otherwise formed to be of a known volume and must be placed on the piston 11 and sized so as to be at least partially exposed to the surrounding medium 25. Preferably, the recess 21 will be placed and sized so as to be completely exposed to the surrounding medium 25 when the piston is in the extended position as shown in FIG. 5. The piston may be formed of other materials than metal such as teflon or other plastic materials. This is true of the cylinder 13 also. The caveat on material selection is that the materials selected for any component of the valve must be compatible with the intended environment in which the valve is to be used so that the environment will not adversely affect the materials and cause a valve failure. This is particularly true in sampling of process streams.

A significant improvement over the prior art for the valve of FIG. 5 resides in the sealing structure. This structure has no dead volume or recesses which can inadvertently collect unknown volumes of sample when the piston is in the extended position. This accomplished by the elimination of multiple O rings for sealing and substitution of a flexible, self compensating sealing arrangement using the property of cold flow of malleable materials to adjust for differences in dimensions of the various components with variations in temperature. The sealing structure is comprised of two sealing rings 17 and 27 of relatively harder materials with a smaller creep rate (non-recoverable strain or permanent percentage deformation or cold flow) separated by and in abutting contact with a cylindrical seal 29 of malleable material of a relatively faster creep rate. A spring 31 applies a constant force to the upper sealing ring 27 biasing it to move toward the sealing ring 17 thereby putting the sealing cylinder 29 in compression stress. This causes the sealing cylinder 29 to attempt to cold flow, i.e., expand in whatever direction is available for expansion in response to the compression stress. If there is any gap between the sidewalls of the piston 11 and the cylindrical seal 29, the cold flow results in radial strain in the cylindrical seal 29 which reduces or eliminates the gap thereby effecting a good seal. Changes in temperature which alter the diameters of the piston 11 and the cylinder 13 (possibly differentially) will not adversely affect the integrity of the seal. This follows because the cold flow strain adjusts for any temperature induced changes in gap size since the pressure exerted by the spring 31 is substantially constant regardless of temperature. Substantially less cold flow in the sealing rings 17 and 27 results because of their relatively harder constitution.

No dead space results in the sealing structure of the invention since there are no gaps between the sealing rings 17 and 27 and the cylindrical seal 29. Further, the seals are affixed to the cylinder and not to the piston, so the seals never are moved by the piston out into the surrounding medium. No spurious, unknown quantities of sample can be accumulated by the seals because of this structure.

The apparatus to move the piston may be any known force producing apparatus such as pneumatic or electrical devices. It is not necessary in the preferred embodiment to know exactly how far the piston moves since the the sample volume is fixed in the recess 21. It is only necessary to know that the piston has been moved to its extended position or to its retracted position.

In the preferred embodiment, the sealing rings 17 and 27 are teflon impregnated with glass graphite or some other material which makes the teflon harder than pure teflon. The sealing cylinder 29 is pure teflon, and has a higher degree of deformability than the sealing rings 17 and 27. These material selections are not critical to the invention however, and any material which is chemically inert, has a low coefficient of friction and which can cold flow will be acceptable for the sealing cylinder 29. The same is true for the material selection of the sealing rings 17 and 27 except that the material must be relatively less deformable than the sealing cylinder 29, or must be capable of being made so with suitable alloying or other techniques.

Figure 7:
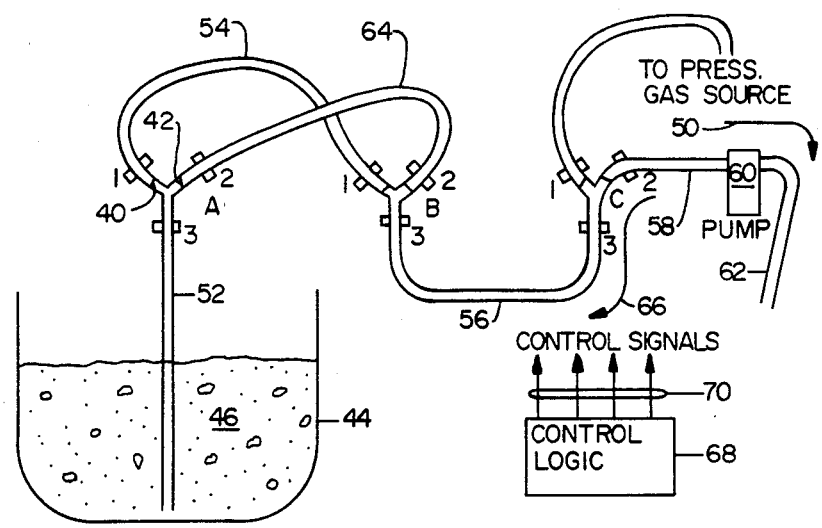
FIG. 7 is a diagram of another, preferred embodiment for a sample metering valve for handling slurry type samples with entrained gas bubbles.

FIG. 7 shows the preferred embodiment for the sample metering valve for slurry or other samples where the volume consumed by gas bubbles is to be eliminated or minimized to improve the accuracy of the volume of the isolated sample. The sample metering valve is actually comprised of three, three-way valves labelled A, B and C in FIG. 7. Each three-way valve is a Y connection with a valve gate such as the gates 40 and 42 in valve A, and each valve A through C has three ports labelled 1 through 3. The gate valves in each valve operate so that at any particular time only one of ports 1 or 2 is coupled to port 3. The connections are as shown in FIG. 7 for the sample metering valve of the preferred embodiment.

The operation of the system to take a sample is as follows. A sample cup 44 is filled with sample 46. Ports 1 on valves A and B are then activated (opened). and port 2 of valve C is activated. A sample pump coupled to port 2 of valve C is then turned on to pump liquid in the direction of arrow 50. This draws sample up into the fill tube 62 and through ports 3 and 1 of valve A, pipe 54, ports 1 and 3 of valve B, pipe 56, ports 3 and 2 of valve C, pipe 58, pump 60 and empty pipe 62. In alternative embodiments, any pumping mechanism or system as long as the loop is completely filled. The pump 60 must be pumped long enough to completely fill the pipe 54 and at least partially fill pipe 56 with enough sample such that when the sample is compressed, the pipe 54 remains filled to capacity. The sample chamber of known volume in the embodiment of FIG. 7 is the pipe 54 plus whatever volume exists in the valves A and B up to the valve plates.

After filling the sample chamber, valve A, port 2 is activated to trap the sample in the pipe 54, and valve C, port 1 is activated to couple pressurized gas into pipe 56. This pressurizes the liquid and gas in the pipes 56 and 54 and thereby compresses any gas bubbles in the pipes 54 and 56 down to zero or small volume. The volume of material in the sample chamber is substantially all liquid by virtue of this pressurization of the lines. Next, valve B, port 2 is activated thereby isolating the sample in the sample chamber 54 between valves A and B. The pump 60 is then activated to pump the remaining sample 46 in the sample cup and any remaining untrapped sample in pipe 56 out of the system through pipe 62. That is, sample is pumped up through fill pipe 52 ports 3 and 2 of valve A, pipe 64, ports 2 and 3 of sample valve B, pipe 56, ports 3 and 2 of valve C, pipe 58, pump 60 and out pipe 62.

Pipe 62 in the preferred embodiment may be coupled alternately to a source of solvent and to a waste dump. Valve C port 2 is reactivated and the pump 60 is then activated to pump solvent in the direction of the arrow 66 to flush out the pipes 56, 64 and 52 and to wash out the remaining sample from the sample cup 44. The pump 60 is then reversed to pump out the solvent in the system and the sample cup in preparation for the dilution.

Next, ports 1 of valves A and B are activated, and the pump 60 is activated to pump in the desired amount of diluent to get the desired sample to diluent concentration. The diluent pumped in in the direction of the arrow 66 flushes the trapped sample out of the pipe 54 down into the sample cup 44. Since the volume of trapped sample is relatively precisely known, good accuracy of the sample concentration may be obtained. Serial dilutions are also possible by repeating the above steps several times to get successively weaker concentrations.

Control logic 68 supplies control signals to all valves and the pump 60 via control bus 70. The control logic 68 may be a programmed digital computer, dedicated combinatorial logic or any other circuit which can cause the above identified algorithm to work. The details of such logic will be apparent to those skilled in the art given the above description of how the system is supposed to operate, and no further details will be given here.

Figure 6:
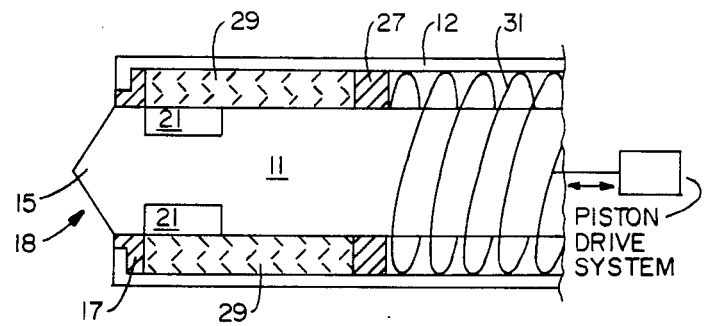
FIG. 6 is a cross sectional view of the sample metering valve of FIG. 5 and shown in the piston retracted position.
Figure 8:
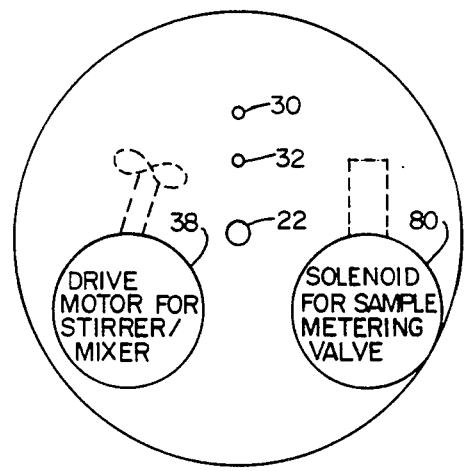
FIG. 8 is a top view of the sample preparation container of FIG. 1.

FIG. 8 is a top view of the sample preparation chamber of FIG. 1 with a round shape assumed. The view of FIG. 8 assumes that a sample metering valve of the type shown in FIGS. 5 and 6 is being used, and that a solenoid 80 is being used to drive the piston 11 in the cylinder 13 of the sample metering valve. The relative arrangement of the various elements of the system are not critical to the practice of the invention, and the arrangement of FIG. 8 is exemplary only.

Although the invention has been described in terms of the preferred embodiment and alternative embodiments disclosed herein, those skilled in the art will appreciate other embodiments which accomplish the same result and which do not depart from the spirit of the invention. All such alternative embodiments are intended to be included within the scope of the claims appended hereto.

What is claimed is:

1. A sample preparation chamber for allowing samples of different compositions to be prepared for assay comprising:

a container having a bottom and walls with at least one region which is lower than all other regions in said bottom, said bottom having a configuration that tends to cause gravity to drive sample in said container to said at least one lower region;

means for mixing non-homogeneous mixtures;

a fill/empty tube entering said container and having an inlet/outlet port located at said at least one lower region; and sample metering means coupled to said container for isolating a known volume of sample from sample in said container and for allowing said known volume to be released back into said container.

2. The apparatus of claim 1 further comprising a means for introducing liquid into said container and spraying said liquid against the walls of said container as it is introduced into said container.

3. The apparatus of claim 1 further comprising a fill pipe means having an output port located in said container but displaced up from the bottom of said container for allowing liquid to be introduced into said container.

4. The apparatus of claim 3 wherein said fill pipe means has a smaller diameter than said fill/empty tube.

5. An apparatus as defined in claim 1 wherein said container comprises a cap and a cup having means for attaching said cup to said cap.

6. The apparatus of claim 5 further comprising a means for introducing liquid into said container and having means for spraying said liquid against the walls of said container as said liquid is introduced into said container.

7. The apparatus of claim 6 further comprising a fill pipe means having an output port located in said container but displaced up from the bottom of said container for allowing liquid to be introduced into said container.

8. The apparatus of claim 7 wherein said means for mixing includes means for grinding solid samples into smaller pieces.

9. A sample preparation chamber for allowing samples of different compositions to be prepared for assay comprising:
- a container comprising a cap and a chemically inert cup having a bottom and walls with at least one region which is lower than all other regions in said bottom, said bottom having a configuration that tends to cause gravity to drive sample in said container to said at least one lower region;
- means for mixing non-homogeneous fluids and for grinding samples into smaller pieces;
- a fill/empty tube having a first diameter entering said container and having an inlet/outlet port located at said at least one lower region;
- sample metering means coupled to said container for isolating a known volume of sample from sample in said cup and for allowing said known volume to be released back into said container; and
- means for spraying the walls of said cup with liquids.

10. The apparatus of claim 9 wherein said cup is lightweight and allows light to pass therethrough.

11. The apparatus of claim 9 wherein said sample metering means comprises:
- means for introducing sample into a chamber of a known volume;
- means for isolating said chamber from the surrounding environment after said sample has been introduced;
- sealing means in said means for isolating to isolate the sample in said chamber without entrapping an unknown volume of sample in the sealing means itself.

12. The apparatus of claim 9 wherein said sample metering means comprises:
- a piston having a sample chamber formed therein having a known volume;
- a cylinder enclosing said piston such that the piston may slide therein, said cylinder having means defining an aperture therein through which said piston may slide so as to expose said chamber to the environment outside said cylinder;
- sealing means for forming a seal between said piston and said cylinder with no areas which can trap sample therein.

13. The apparatus of claim 9 wherein said sample metering means comprises:
- means for pumping precisely controlled, user defined amounts of liquid into or out of a first system port;
- means for supplying pressurized gas or liquid to a second system port;
- a container for storing sample and diluted sample;
- valve means having at least two states for allowing said pumping means to pump sample out of said container into a sample chamber which may be selectively coupled to either said first or said second system port and for allowing sample in said sample chamber to be isolated from said container and both said first and second system ports and for allowing sample in said sample chamber to be placed back into said container, said valve means having control inputs for controlling which of said at least two states said valve means is in; and
- control means for causing said valve means to be in one of said at least two states in a predetermined sequence.

14. The apparatus of claim 13 wherein said control means also causes said means for supplying pressurized gas or liquid to pressurize the sample in said sample chamber before said sample is isolated so as to compress any gas bubbles trapped in said sample.

* * * * *